US00PP07901P

United States Patent [19]

Twomey

[11] Patent Number: Plant 7,901

[45] Date of Patent: Jul. 7, 1992

[54] ROSE PLANT NAMED TWOBE

[75] Inventor: Jerry Twomey, Leucadid, Calif.

[73] Assignee: DeVor Nurseries, Inc., Watsonville, Calif.

[21] Appl. No.: 611,512

[22] Filed: Nov. 13, 1990

[51] Int. Cl.[5] ..... A01H 5/00

[52] U.S. Cl. ..... Plt./18

[58] Field of Search ..... Plt./11, 18, 19, 20

*Primary Examiner*—Howard J. Locker

*Attorney, Agent, or Firm*—Charles W. Rummler

[57] ABSTRACT

A new and distinct rose plant suitable for both greenhouse and garden culture and particularly distinguished by its continuous and profuse production of very large flowers having in general a Neyron Rose to Rhodonite Red coloration from early Spring into Fall, blooming freely under natural conditions and born on strong, vigorous upright stems of substantial length on a very tall plant having a vigorous and sturdy growth habit with abundant foliage.

1 Drawing Sheet

BACKGROUND OF THE NEW PLANT

My new variety of rose plant originated as a hybrid seedling produced at Carlsbad, Calif. by crossing the variety 'Pristine' U.S. Plant Pat. No. 3,997 with the variety 'Fortuna' (unpatented) with the object of producing an improved show bloom having improved health, vigor and production. The selected seedling appeared to very well achieve my objectives and accordingly I propagated the seedling by means of cuttings as well as by budding at Pleasanton, Calif. with very satisfactory results and at my direction such propagation was carried on through several successive generations which demonstrated conclusively that the novel characteristics of this new plant would hold true from generation to generation and appeared to be firmly fixed.

DESCRIPTION OF THE DRAWING

This new rose plant is illustrated by the accompanying photographic drawing which, in full color, shows a face view of a fully opened bloom demonstrating the flower form and its petalage, the color shown being as nearly true to those herein specified as is reasonably possible to obtain by conventional photographic procedures.

DESCRIPTION OF THE NEW VARIETY

The following is a detailed description of my new rose plant based upon observation of plants grown in greenhouse and out of doors at Pleasanton, Calif. with color designations according to The R.H.S. Color Chart published by The Royal Horticultural Society of London, England.

THE PLANT

Origin: Seedling.
Parentage:
*Seed parent.*—'Pristine' U.S. Plant Pat. No. 3,997.
*Pollen parent.*—'Fortuna' (unpatented).
Classification:
*Botanic.*—Rosa-hybrid.
*Commercial.*—Garden rose plant.
Form: Upright bush.
Height: About 150 cm.
Main stem:

*Length.*—About 75 cm. from the last flower cut.
*Color.*—Yellow Green 146-B.
Branching character: Free branching.
Growth habit: Vigorous, upright and very sturdy.
Foliage:
*Quantity.*—Abundant.
*Number of leaves.*—8 or 9 from last flower cut.
*Shape.*—Odd pinnate.
*Size.*—About 130 mm. long, in average.
Leaflets:
*Number.*—3 and 5.
*Shape.*—Ovate with denticulate margin.
*Texture.*—Leathery.
*Aspect.*—Smooth and glossy.
*Color.*—Upper side — Yellow Green 147-A. Under side — Yellow Green 148-B.
*Stipules.*—Adnate and tipped with glands.
*Rachis.*—133 mm. on 5 part leaf and 94 mm. on 3 part leaf.
*Petioles.*—Length: About 14 to 16 mm.
Ribs and veins: Slightly depressed on top side and rounded on the under side.
Thorns: Slightly curved and varying in size.
*Color.*—Greyed Red 181-C.
*Size.*—About 8 mm. long.

THE BUD

Size: Medium.
*Diameter.*—About 28 mm.
*Length.*—About 33 mm.
Shape: Medium and pointed.
Color of petals:
*When sepals first divide.*—Red group 48-C.
*When petals begin to unfurl.*—Red group 51-D.
Sepals:
*Number.*—5.
*Character.*—Spreading with some leaf pointed, hooded over the bud and curled back when flowers open.
*Color.*—Inside — Greyed Purple 187-D with Yellow Green 146-C nearing the tip and all covered with small White hairs.
Calyx:
*Shape.*—Funnel-shaped.
*Size.*—Large with breadth of 15 mm. and length of about 9½ mm.
*Aspect.*—Smooth.

*Splitting.*—The calyx does not split.

Peduncle of flower stem:

*Length.*—About 97 mm.

*Character.*—Rigid, erect and sturdy.

*Color.*—Greyed Red 178-A with undertones of Yellow Green 144-A.

THE FLOWER

Blooming habit: Continuous and profusely from early Spring through Fall, blooming freely under natural conditions.

Size of bloom: Very large.

*Diameter.*—About 84 mm.

*Depth.*—41 mm.

Borne: Singly on long, strong stems.

Shape:

*When bloom first opens.*—Slightly cup shaped with high center.

*When bloom matures.*—Very nicely imbricated.

Petalage:

*Number.*—35 to 40.

*Arrangement.*—Imbricated.

*Form.*—Spoon shaped and imbricated with slightly lobed margins.

*Texture.*—Semi-leathery and soft.

*Aspect.*—Semi-velvety.

*Color.*—Outer petals: Body — Neyron Rose 55-B tinged with 56-A. Reverse side: Body — center White with a Pink tinge and Red Purple margin 68-A. Inside petals: Body — 51-D fading to 49-C with Yellow base 2-C turning to Yellow 6-A. Reverse side: Red Purple 64-C at margin and 62-D going into White 155-D. Base — Yellow 10-C.

*Petaloids.*—Number: 4 to 6. Size: About 17 mm. long. Color: Body — Red 54-D with Yellow base 3-A.

Discoloration after full bloom: Discolors to Red 49-C.

Persistence: The flower petals will drop clean.

Disease resistance: Moderately resistant to mildew, rust and black spots with a strong resistance to botrytis as observed at Watsonville, Calif.

Fragrance: Mild to strong musk fragrance.

Lasting quality: Long lasting on the plant and as a cut flower.

THE REPRODUCTIVE ORGANS

Stamens:

*Number.*—198 to 216.

*Arrangement.*—Introrse.

*Anthers.*—Size: 2 to 3 mm. Color: Yellow 20-A.

*Filaments.*—Length: 7 to 8 mm. Color: Yellow Orange 15-D.

*Pollen.*—Color: Yellow Orange 20-A.

Pistils:

*Number.*—209 to 218.

*Styles.*—Length: About 17 mm. Color: Red Purple 61-D.

*Stigmas.*—Color: Yellow 10-C.

Character of the ovaries: Small, oblong and rounded around the edges, all covered with silvery hairs.

THE FRUIT

Fertility: The fruit is fertile.

Shape: Pear shaped.

Color: Yellow Orange 21-A.

The present variety carries the vigor and reliability of its seed parent 'Pristine' but is more double, slower opening, longer lasting, the petals are broader and dropping cleaner when aged.

I claim:

1. The new and distinct rose variety substantially as herein shown and described, characterized by its continuous and profuse production of very large blossoms having a light pink coloration blooming from early spring to late Fall on long, strong, upright stems of a plant having a vigorous and free branching growth habit with abundant foliage.

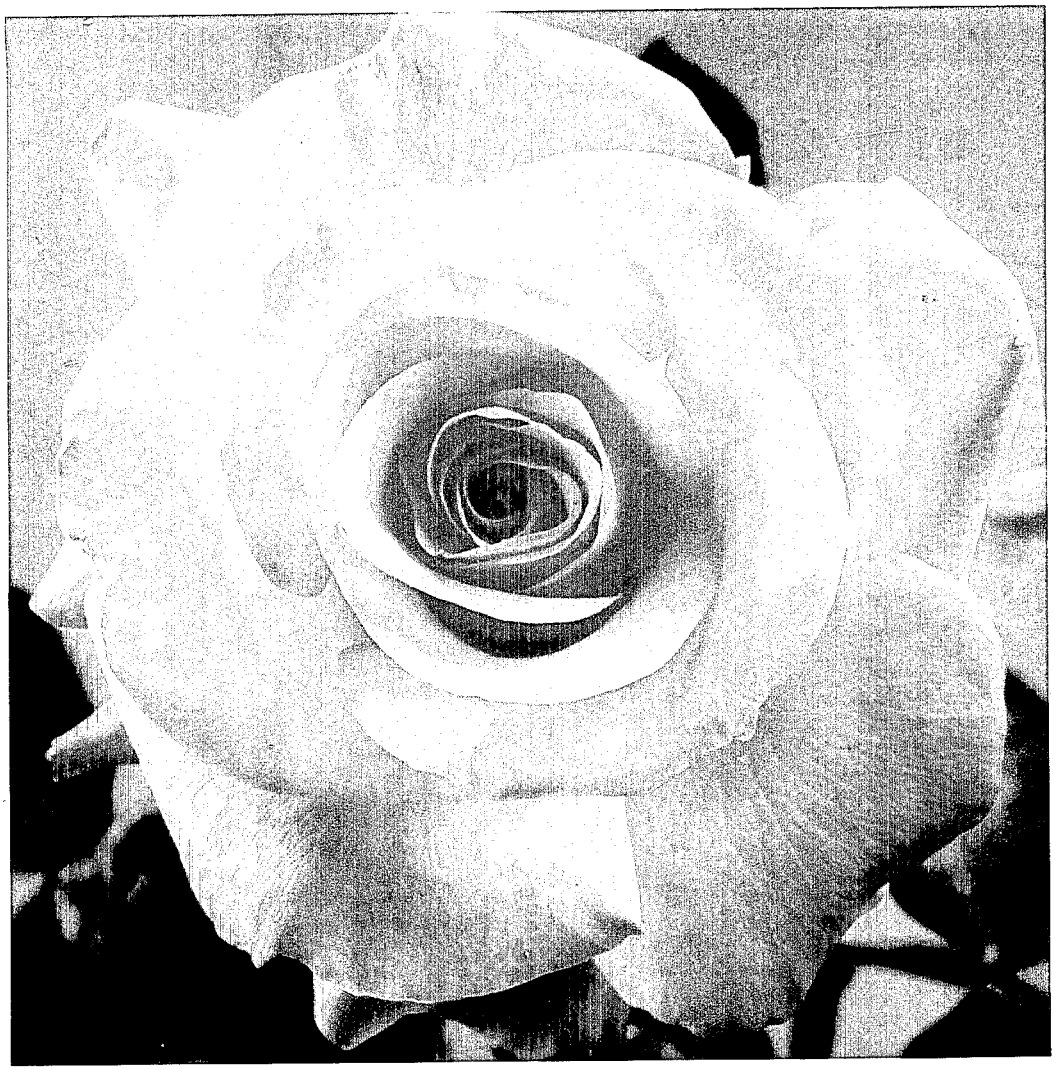

* * * * *